United States Patent
Pereira et al.

(10) Patent No.: US 10,856,815 B2
(45) Date of Patent: Dec. 8, 2020

(54) GENERATING NATURAL LANGUAGE REPRESENTATIONS OF MENTAL CONTENT FROM FUNCTIONAL BRAIN IMAGES

(71) Applicant: Siemens Medical Solutions USA, Inc., Malvern, PA (US)

(72) Inventors: Francisco Pereira, Jersey City, NJ (US); Bin Lou, West Windsor, NJ (US); Angeliki Lazaridou, Artemida (GR)

(73) Assignee: Siemens Medical Solutions USA, Inc., Malvern, PA (US)

( * ) Notice: Subject to any disclaimer, the term of this patent is extended or adjusted under 35 U.S.C. 154(b) by 242 days.

(21) Appl. No.: 15/752,276

(22) PCT Filed: Oct. 21, 2016

(86) PCT No.: PCT/IB2016/001517
§ 371 (c)(1),
(2) Date: Feb. 13, 2018

(87) PCT Pub. No.: WO2017/068414
PCT Pub. Date: Apr. 27, 2017

(65) Prior Publication Data
US 2019/0380657 A1 Dec. 19, 2019

Related U.S. Application Data

(60) Provisional application No. 62/245,593, filed on Oct. 23, 2015, provisional application No. 62/249,825, filed on Nov. 2, 2015.

(51) Int. Cl.
*A61B 5/00* (2006.01)
*A61B 5/055* (2006.01)
(Continued)

(52) U.S. Cl.
CPC .......... *A61B 5/7267* (2013.01); *A61B 5/0042* (2013.01); *A61B 5/0263* (2013.01);
(Continued)

(58) Field of Classification Search
CPC . A61B 2576/026; A61B 34/10; A61B 5/0042; A61B 5/0263; A61B 5/04842;
(Continued)

(56) References Cited

U.S. PATENT DOCUMENTS

2008/0270120 A1\* 10/2008 Pestian ............... G06F 17/2785
704/9
2011/0301431 A1 12/2011 Greicius et al.
(Continued)

FOREIGN PATENT DOCUMENTS

CN 104391963 A 3/2015

OTHER PUBLICATIONS

Extended European Search Report (EESR) dated May 21, 2019 in corresponding European patent application No. 16856986.1.
(Continued)

*Primary Examiner* — Angela A Armstrong (57) ABSTRACT

By way of introduction, the present embodiments described below include apparatuses and methods for generating natural language representations of mental content from functional brain images. Given functional imaging data acquired while a subject reads a text passage, a reconstruction of the text passage is produced. Linguistic semantic vector representations are assigned (1301) to words, phrases or sentences to be used as training stimuli. Basis learning is performed (1305), using brain imaging data acquired (1303) when a subject is exposed to the training stimuli and the corresponding semantic vectors for training stimuli, to learn an image basis directly. Semantic vector decoding (1309) is performed with functional brain imaging data for test stimuli
(Continued)

and using the image basis to generate a semantic vector representing the test imaging stimuli. Text generation (1311) is then performed using the decoded semantic vector representing the test imaging stimuli.

14 Claims, 9 Drawing Sheets

(51) Int. Cl.
*A61B 5/0484* (2006.01)
*A61B 5/026* (2006.01)
*G06F 17/27* (2006.01)
*G16H 30/40* (2018.01)
*G06N 3/08* (2006.01)
*G06F 40/30* (2020.01)

(52) U.S. Cl.
CPC .......... *A61B 5/04842* (2013.01); *A61B 5/055* (2013.01); *G06F 40/30* (2020.01); *G06N 3/08* (2013.01); *G16H 30/40* (2018.01)

(58) Field of Classification Search
CPC ..... A61B 5/055; A61B 5/7267; A61B 5/0022; A61B 5/4064; A61B 5/7246; A61B 5/7264; G06F 17/2785; G06F 3/015; G06F 40/30; G06N 3/08; G16H 30/40; G16H 50/20; G16H 50/50; G16H 50/70; G01R 33/4806; G06K 2209/05; G06K 9/6247; G06K 9/6269; G06T 2207/20081; G06T 7/0012
See application file for complete search history.

(56) References Cited

U.S. PATENT DOCUMENTS

2013/0178733 A1 7/2013 Langleben
2013/0184558 A1* 7/2013 Gallant ................ A61B 5/0042
                                                          600/409
2013/0246322 A1* 9/2013 De Sousa Webber ......................
                                                          G06N 3/0454
                                                          706/18
2015/0269139 A1* 9/2015 McAteer ............. G06F 17/2785
                                                          704/9
2018/0092567 A1* 4/2018 Nishimoto ........... A61B 5/7267

OTHER PUBLICATIONS

Pereira et al: "Generating Text from Functional Brain Images"; 2011; Frontiers in Human Neuroscience, vol. 5; 31, pp. 1-11
Francisco Pereira et al: "Generating Text from Functional Brain Images"; Frontiers in Human Neuroscience, vol. 5; pp. 1-11; XP055362470; DOI: 10.3389/fnhum.2011.00072 / Jan. 1.
Anderson et al: "Reading visually embodied meaning from the brain: Visually grounded computtional models decode visual—object mental imagery induced by written text"; 2015; vol. 120; pp. 309-322, XP029282531; ISSN: 1053-8119; DOI: 10.1016/J. NEUROIMAGE.
Fyshe et al: "Interpretable Semantic Vectors from a Joint Model of Brain- and Text-Based Meaning"; 2014; pp. 489-499; XP055520439; DOI: 10.3115/v1/P14-1046; Proceedings of the 52nd Annual Meeting of the Association for Computational Linguistics (vol. 1:Long Papers): / Jan. 1, 2014.
Shinkareva S V et al: "Commonality of neural representations of words and pictures"; 2011; Neuroimage, Elsevier; vol. 54, No. 3; pp. 2418-2425; XP027564712; ISSN: 1053-8119 / Jan. 2, 2011.
Simanova et al: "Modality-Independent Decoding of Semantic Information from the Human Brain"; 2014; vol. 24, No. 2; pp. 426-434; XP055585459; ISSN: 1047-3211; DOI: 10.1093/cercor/bhs324 / Jan. 2, 2014.
International Search Report dated Jul. 10, 2017 in corresponding International Application No. PCT/IB2016/001517.
S. M. Smith, et al., "Advances in functional and structural MR image analysis and implementation as FSL," NeuroImage 23, pp. S208-S219, 2004.
K. J. Friston, et al.; (Eds.) Statistical Parametric Mapping: The Analysis of Functional Brain Images, Academic Press, 2007.
Chinese Office Action dated Mar. 31, 2020 in corresponding Chinese Patent Application No. 201680061939.6.

* cited by examiner

GENERATING NATURAL LANGUAGE REPRESENTATIONS OF MENTAL CONTENT FROM FUNCTIONAL BRAIN IMAGES

CROSS-REFERENCE TO RELATED APPLICATIONS

The present patent document claims the benefit of U.S. Provisional Application No. 62/245,593, filed on Oct. 23, 2015, and U.S. Provisional Application No. 62/249,825, filed on Nov. 2, 2015 which are hereby incorporated by reference in its entirety.

RESEARCH AGREEMENT

This research is based upon work supported in part by the Office of the Director of National Intelligence (ODNI), Intelligence Advanced Research Projects Activity (IARPA), via Air Force Research Laboratory (AFRL), under contract no. FA8650-14-C-7358. The government has certain rights in the invention.

BACKGROUND

The present embodiments relate to decoding mental content from functional brain images. The most common form of brain decoding determines which stimulus out of a limited set of stimuli was shown to a subject using brain imaging. Conversely, generative brain decoding generates an entire artifact to represent mental content, and attempts to reconstruct the actual stimulus shown (e.g., pictures or video). Generative brain decoding is restricted to mental content as a result of visualization by the subject, and requires a database with most conceivable stimuli. The database requirement is not feasible for language text. Alternatively, the artifact could be a construct representing a complex mental state, such as a cloud of words sized by their probability of being in the subject's mind.

Introducing strong priors in the decoding process has been experimentally shown to be beneficial in diverse decoding scenarios. For example, constraints are imposed when reconstructing video from brain activities. First, available video frames are ranked in a database with respect to their similarities to the evoked brain activation. Then, the top k most similar video frames are combined linearly to obtain the reconstructed video. Generation, using a quantitative representation derived from text corpora, may be constrained to avoid generating inconsistent word clouds.

SUMMARY

By way of introduction, the present embodiments described below include apparatuses and methods for generating natural language representations of mental content from functional brain images. Given functional imaging data acquired while a subject reads a text passage, a reconstruction of the text passage is produced. Linguistic semantic vector representations are assigned to words, phrases or sentences to be used as training data. Basis learning is performed to learn an image basis directly. The basis learning uses brain imaging data acquired when a subject is exposed to the training data and using the corresponding semantic vectors for training data. Semantic vector decoding is performed with functional brain imaging data for test data and using the image basis to generate a semantic vector representing the test imaging data. Text generation is then performed using the decoded semantic vector representing the test imaging data.

In a first aspect, a method for generating natural language representations of mental content from functional brain images is provided. The method includes capturing a first set of functional brain imaging data while a subject is exposed to a plurality of stimuli and generating basis images by mapping semantic vector representations of the plurality of stimuli to spatial patterns of activation in the first set of functional brain imaging data. The method also includes capturing a second set of functional brain imaging data while a subject is exposed to a test stimuli and generating a semantic vector representation for the test stimuli using the basis images and spatial patterns of activation in the second set of functional brain imaging data.

In a second aspect, a system for generating natural language representations of mental content from functional brain images is provided. The system includes a linguistic semantic vector representor configured to assign semantic vectors to training text and a basis learner configured to map the semantic vectors to a first set of functional brain imaging data acquired in the presence of the training text. The system also includes a semantic vector decoder configured to decode a semantic vector from a second set of functional imaging data and a text generator configured to generate a text output based on the decoded semantic vector.

In a third aspect, a method for generating natural language representations of mental content from functional brain images is provided. The method includes assigning semantic vector representations to a plurality of stimuli and generating basis images by the mapping semantic vector representations of the plurality of stimuli to spatial patterns of activation in a first set of functional brain imaging data. The method also includes generating a semantic vector representation for a test stimuli using the basis images and spatial patterns of activation in a second set of functional brain imaging data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EXEMPLARY EMBODIMENTS

The present embodiments relate to decoding generic mental content from functional brain images into a form or representation that is understandable by humans. The present embodiments model how stimuli, such as text passages, are processed by the human brain. Models are built by acquiring brain imaging data while a subject mentally processes one of set of stimuli, and the models are used to decode the mental content from a brain imaging acquired while subjects process a different set of stimuli. For example, using known training data, the model is trained to decode brain imaging data captured while the subject is exposed to unknown and/or testing data.

Figure 1:
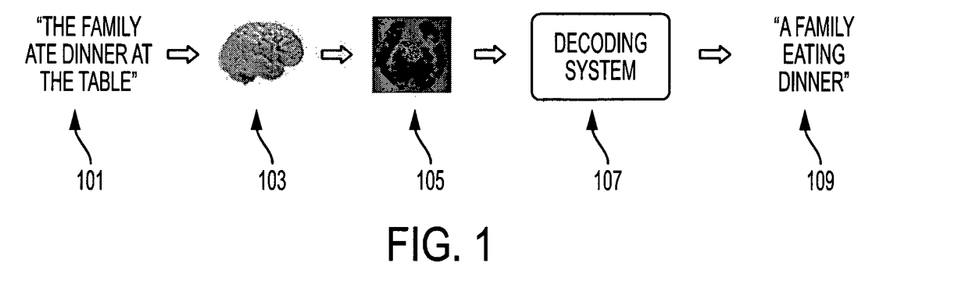
FIG. 1 illustrates an embodiment for generating natural language representations of mental content from functional brain images.

The present embodiments may also produce natural language sentences describing mental content. For example, a quantitative representation of mental content is generated and a separate model produces sentences from those quantitative representations. FIG. 1 illustrates an embodiment for generating natural language representations of mental content from functional brain images.

Referring to 101, a vector representation is assigned to training data. In this example, the training data is text in the form of the sentence "The family ate dinner at the table." Other types of training data may be used, such as imagery, sound or other sensory-based training data. For example, instead of the sentence in the example above, a photograph, video or other imagery of a family eating dinner at a table may be used. A quantitative representation of the training data may be a semantic vector representation. For example, the semantic vector representation may be a multidimensional vector. In an example, each word in the sentence of the training data is assigned a multidimensional semantic vector representation. Alternatively or additionally, the vector representations for each word of the sentence may be averaged to assign a single vector representation for the entire sentence, or another method used to directly produce a vector representation for the sentence.

At 103, the subject processes the training stimuli while functional brain imaging is acquired. For example, the training stimuli are presented to the subject while being monitored by functional brain imaging; one form of presentation could be allowing the subject to read the sentence text. The functional brain imaging may be functional magnetic resonance imaging (fMRI) or another imaging modality such as magnetoencephalography (MEG), electroencephalography (EEG) or electrocorticography (ECoG).

At 105, the functional brain imaging is mapped to a vector representation of the training data. When the subject processes the training stimuli, a unique spatial pattern of activation is captured by the functional brain imaging. For example, using fMRI, brain activity is detected by monitoring changes in blood flow in different regions of the subject's brain representing activity in those areas of the brain. The spatial pattern of the brain activity is mapped to the vector representation of the training stimuli to generate an image basis for the patterns of brain activity. For example, each dimension of a multidimensional linguistic semantic vector representation is mapped to the fMRI image data. By finding common characteristics between patterns of brain activity that parallel those of training stimuli with common characteristics in their vector representations, the generated basis images are used to teach the system how to decode mental content in the subject's brain. For example, vector representations of training data may overlap when the training data is similar in context and/or meaning. A decoding system is thus a combination of fixed procedures and components learned from training stimuli and corresponding brain images.

At 107, mental content for a new or current subject is decoded using the decoding system based on the image basis. For example, mental content is decoded from functional brain imaging acquired of the subject while the subject is exposed to test stimuli. The test stimuli are unknown to the system, however the test data may be the same or similar to the training data. The functional brain imaging is acquired for the new or current subject using fMRI, and based on the image data, a vector representation is decoded from the image data. At 109, text is generated from the decoded mental content. For example, natural language sentences describing the mental content are generated from the vector representations of the mental content. In this example, the natural language sentence generated is "A family eating dinner."

By training the system with many different sets of training stimuli, and determining common characteristics between the brain activity and the vector representations of the training data, the system is capable of generating natural language text when the subject is exposed to diverse test stimuli. The system can then be applied to new imaging data, to generate a linguistic output.

According to an embodiment, the system may be hardware, software or a combination of hardware and software, including four modules: a linguistic semantic vector representation module; a basis learning module; a semantic vector decoding module; and a text generation module. The modules are initially calibrated using a text corpus and a set of brain images for which the originating stimuli are known. The text corpus and the set of brain images are used to build a forward model of brain activation. A new set of brain images are used with a reverse model of brain activation to generate a text prediction.

Figure 2:
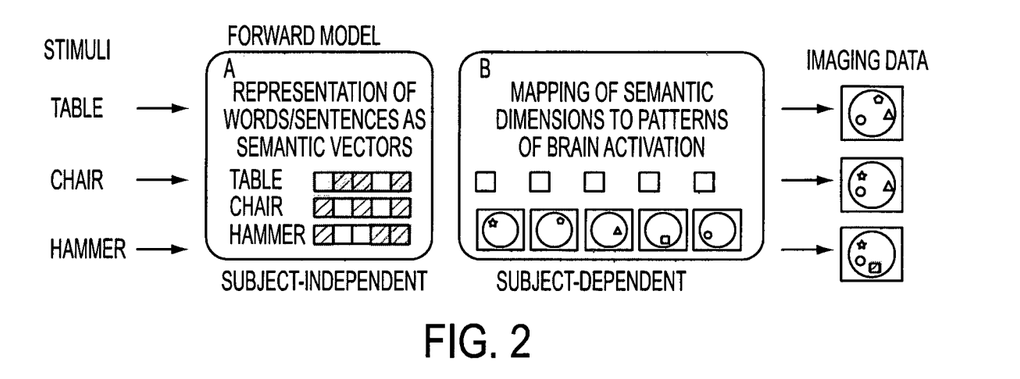
FIG. 2 illustrates an embodiment of a forward model of brain activation for known stimuli.

FIG. 2 illustrates an embodiment of a forward model of brain activation for known stimuli. Many different known stimuli may be used. In this example, a subset of the stimuli is depicted, including text for the words "table," "chair" and "hammer." Imaging data, depicted on the right of FIG. 2, is acquired while subjects are exposed to the stimuli. The forward model maps, or connects, stimulus concepts with corresponding patterns of brain activation. As depicted in FIG. 2, a subject-independent component (A) provides a mapping between each word's naming stimulus concept and a respective 300-dimensional semantic vector for each word (only five dimensions are depicted in the FIG. 2 as five blocks for each word). The subject-dependent component (B) provides a mapping between the presence of each semantic dimension and the dimension's influence in the pattern of brain activation (represented schematically as geometric shapes in the FIG. 2).

Generating natural language representations of mental content from functional brain images may overcome limitations in the related art. The present embodiments may decode any type of content, abstract or concrete, given the semantic representations assigned to the meaning of arbitrary words and/or combinations of words. The present embodiments may only require enough brain imaging data to calibrate and train the forward model. Further, text generation may be trained entirely based on linguistic data from text corpora (e.g., text available online). Additionally, due to the generative process of the text generation, the present embodiments are capable of producing novel sentences that have never been encountered in the text corpus used for calibration and training. Finally, the model is not tied to any specific type of input and may work with any semantic vectors from any source (e.g., other imaging modalities, text, etc.).

As discussed above, the present embodiments may include a linguistic semantic vector representor, a basis learner, a semantic vector decoder and a text generator. For example, the linguistic semantic vector representor, the basis learner, the semantic vector decoder and the text generator may be configured as hardware and/or software modules.

Figure 3:
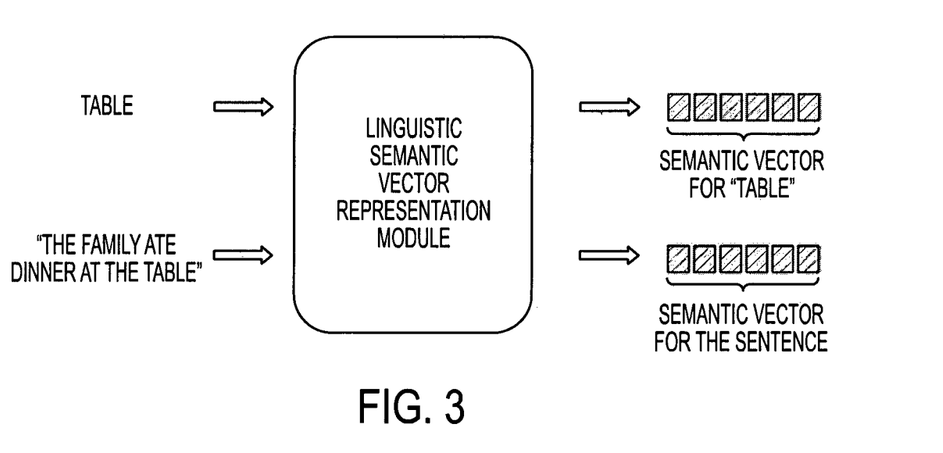
FIG. 3 illustrates an embodiment for assigning a semantic vector to known stimuli.

FIG. 3 illustrates an embodiment for assigning a semantic vector to known stimuli. As depicted in FIG. 3, a linguistic semantic vector representation module is provided. The linguistic semantic vector representation module assigns a semantic vector to words, phrases and/or sentences used as stimuli (e.g., training data), as depicted in element A of FIG. 2. The linguistic semantic vector representation module uses many documents as a text corpus to identify similarities in context and meaning between words with unrelated spelling and other characteristics. For example, referring to FIG. 2, similarities in context may be identified for "table" and "chair," while no similarities in context are identified between "chair" and "hammer." The semantic vector representations may be multidimensional vectors, such as a 300-dimensional semantic vector for each word. The number of dimensions may be varied based on the implementation.

In an embodiment, Global Vectors for Word Representation (GloVe vectors) are used to represent individual words and averaging of vectors for the content words in a sentence to represent it. GloVe is an unsupervised learning algorithm that may be used to obtain vector representations for words. Training is performed on aggregated global word-word co-occurrence statistics from a corpus, and the resulting vector representations provide linear substructures of the word vector space (e.g., context and meaning of the words). The programmer may select any corpus. In another embodiment, Skip-Thought vectors are used. Additional or different vector representations of training stimuli may be used to assign semantic vectors to the known stimuli.

Figure 4:
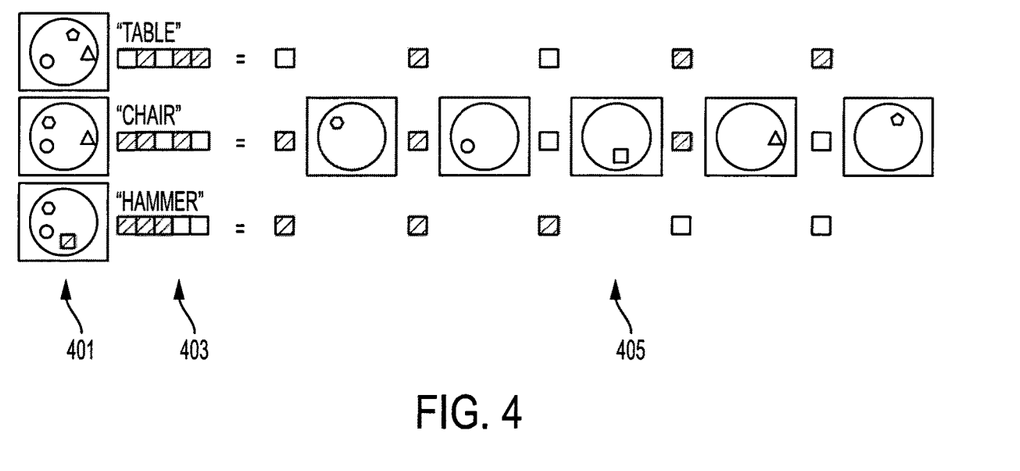
FIG. 4 illustrates an embodiment for learning an image basis.

FIG. 4 illustrates an embodiment for learning an image basis. As depicted in FIG. 4, a basis learning module is provided. The basis learning module receives semantic vector representations for words or sentences used as stimuli and brain imaging data acquired while a subject is exposed to the stimuli. The basis learning module then uses vector representations and the brain imaging data to learn an image basis. The image basis is a mapping between the presence of each dimension of the semantic vector and a manifestation of the dimension in the spatial pattern of activation in the functional brain imaging data, as depicted in element B of FIG. 2.

As illustrated in the FIG. 4, schematic brain images 401 are depicted (simplified for this illustration) with shapes corresponding to patterns of activation corresponding to brain activity as a result of the subject being exposed to the known stimuli. The multidimensional vector representations 403 are depicted (simplified as five dimension vectors for this illustration) representing various words used as the known stimuli. The module learns the image basis 405 identifying common characteristics between the patterns of activation in the schematic brain images 401 as a result of exposure to different words with semantic vectors having common characteristics (i.e., presence of the same semantic dimensions, in this example, or similar values for some semantic dimensions, in general).

In an embodiment, ridge regression is used to factorize a brain imaging data matrix (#stimuli×#voxels) into a product of a semantic vector matrix (#stimuli×#semantic dimensions) and an unknown basis matrix (#semantic dimensions× #voxels). The ridge penalty parameter is set using generalized cross-validation. Other factorization algorithms may be used, such as different types of regularization. For example, L1 regularized logistical regression and singular value decomposition (SVD) of the semantic vector matrix may be used.

Figure 5A:
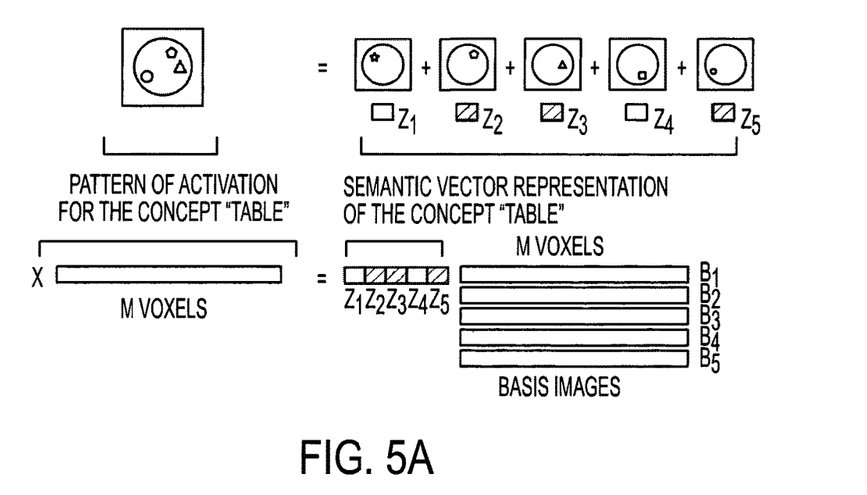
FIG. 5A illustrates an embodiment for representing a functional brain image as a linear combination of images in an image basis, by representing the image as a vector resulting of the product of a semantic vector and a matrix whose rows are vector representations of basis images.
Figure 5B:
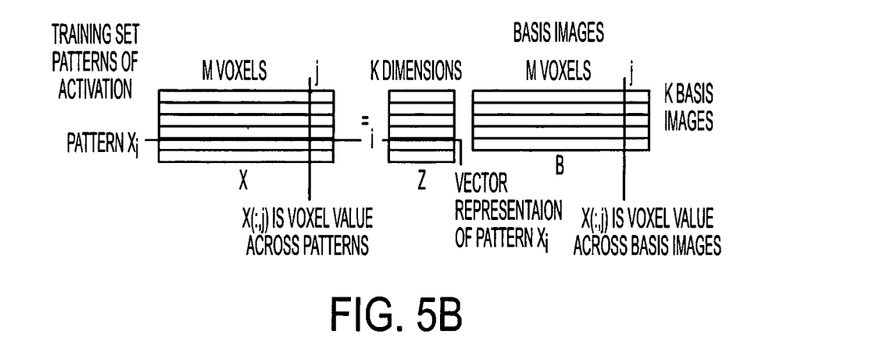
FIG. 5B illustrates an embodiment for learning the representation of each voxel j in the training brain images as the product of matrix of semantic vectors and the value of voxel j in all basis images.
Figure 5C:
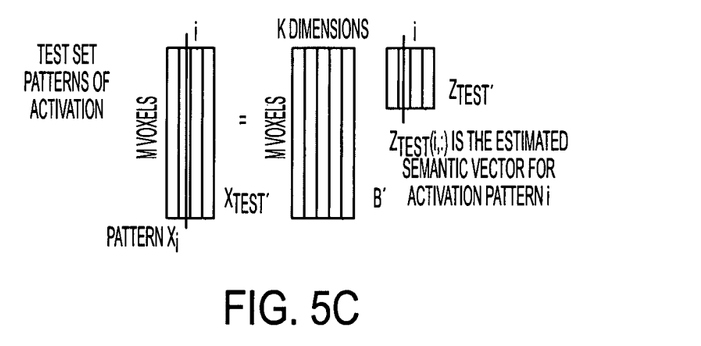
FIG. 5C illustrates an embodiment for generating a semantic vector representation of test brain images, given an image basis.

FIGS. 5A-5C illustrate an embodiment for generating semantic vector representations of mental content from functional brain images using image basis. The top of FIG. 5A depicts a captured brain image corresponding to the concept "table." The brain image is decomposed into a weighted combination of simpler patterns captured by each basis image. The combination weights are mapped to corresponding values in each dimension of a semantic vector representing "table." In this example, the #semantic dimensions is 5. The bottom of FIG. 5A the brain image expressed as a vector x with as many entries as voxels. Each image vector x is expressed as a linear combination of basis images (e.g., images $b_1, \ldots, b_5$) of the same dimensionality, with the weights given by the semantic feature vector $z=[z_1, \ldots, z_5]$.

FIG. 5B depicts an example of basis learning. Patterns of activation for multiple concepts (rows of matrix X, #stimuli×#voxels) are represented as a factorization of matrix X into the product of: known matrix Z (#stimuli× #semantic dimensions, where the rows are the semantic vector representations of each concept); and unknown basis matrix B (#semantic dimensions×#voxels, where the rows are the patterns in the basis). In FIGS. 5A-5C, columns and rows of the matrices are referred to using the following notation: X(:,j) for column j of matrix X; and X(i,:) for row i of matrix X. Further, vectors and matrices are referred to using the following notation: x' indicates the transpose of vector x; and X' indicates the transpose of matrix X. In this example, learning the basis matrix B is decomposed into a set of #voxels independent regression problems. For example, one regression problem is performed per voxel j for the values of voxel j across all images. The column j for matrix X, X(:,j), are predicted from Z using regression coefficients B(:,j) representing the values of voxel j across basis images.

Figure 6:
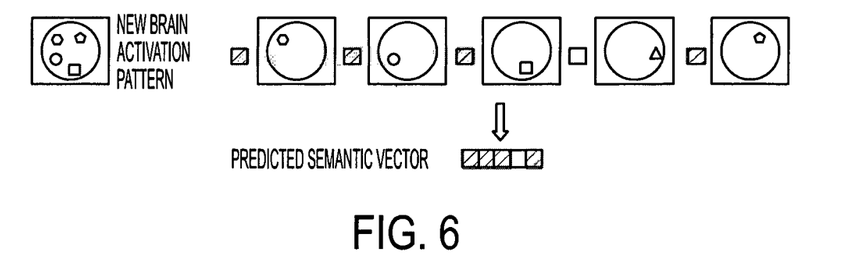
FIG. 6 illustrates an embodiment for predicting a semantic vector from a brain activation pattern, by expressing it as a linear combination of basis images where the combination coefficients are the entries in the semantic vector.

FIG. 6 illustrates an embodiment for predicting a semantic vector from a brain activation pattern. As depicted in FIG. 6, a semantic vector decoding module is provided. The semantic vector decoding module receives, as an input, functional brain imaging data acquired as the subject is exposed to the testing stimuli. Using the image basis learned by the basis learning module, the semantic vector decoding module generates a semantic vector representing the testing stimuli. By representing the test imaging data in the image basis, the resulting coefficients provide a semantic vector for the test imaging data.

In this embodiment, a ridge regression is used to factorize the test data as a product of the basis image matrix and an unknown semantic vector. The mathematical underpinnings of this embodiment are the same as used for the linguistic semantic vector representation module, reversing the forward model.

Referring back to FIGS. 5A-5C, FIG. 5C depicts an example of estimating a semantic vector $Z_{test}$ for patterns of brain activation in the test imaging data set $X_{test}$, given basis images B. In this example, estimating the semantic vector $Z_{test}$ is decomposed into a set of n test independent regression problems, where x' is predicted from B' using regression coefficients $z'=[z_1, \ldots, z_5]'$. The basis learning and semantic vector estimation may require regularization because there are often more semantic space dimensions than examples, with either the dimensions or the basis images being collinear.

Figure 7:
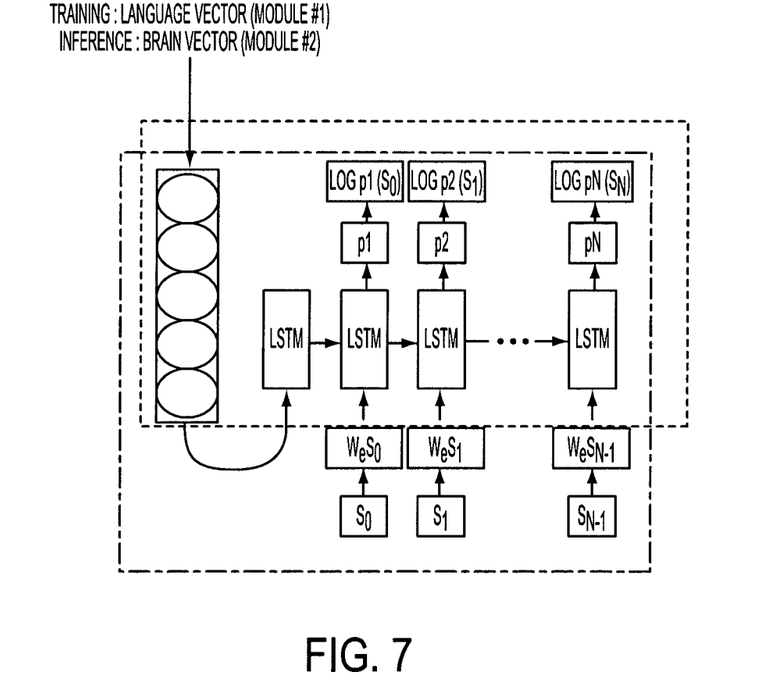
FIG. 7 illustrates an embodiment of generating text from semantic vector representations of mental content.

FIG. 7 illustrates an embodiment of generating text from semantic vector representations of mental content. As depicted in FIG. 7, a text generation module is provided. In this embodiment, the text generation module is based on training a Recurrent Neural Network. For example, the text generation module is trained with many different semantic vectors associated with known text. Other machine learning and data mining may be used for text generation by training for generating text from semantic vectors.

Referring to FIG. 7, the text generator may include two modules: a training module and an inference module. For example, the training module trains the text generator, and the inference module generates text for the text generator. The training model receives an input of size N derived from a text corpus D in the form of pairs (s_i, v_i), where v_i is a semantic vector representation of a sentence s_i assigned by the semantic vector representation module. The parameters \theta of the model are estimated such that, given the vector v_i, the reconstructed sentence s_i is as accurate as possible, as measured with a cross-entropy or other criterion. The inference model receives a semantic vector v_j, decoded with the semantic vector decoding module, and produces a sequence of words forming a predicted sentence for the received semantic vector v_j.

Figure 8:
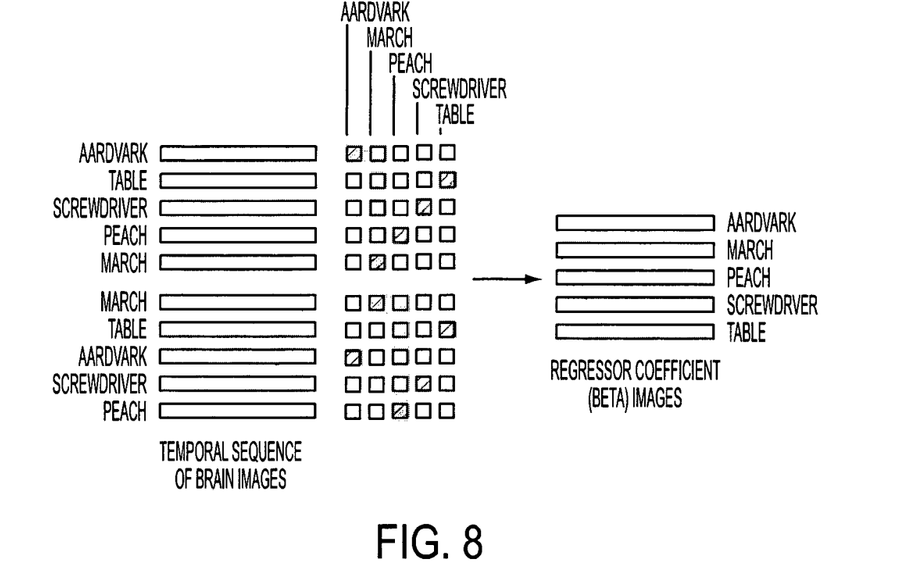
FIG. 8 illustrates an embodiment of using a general linear model to deconvolve the response to individual stimuli from a temporal sequence of brain images captured as those stimuli were shown to a subject.
Figure 9:
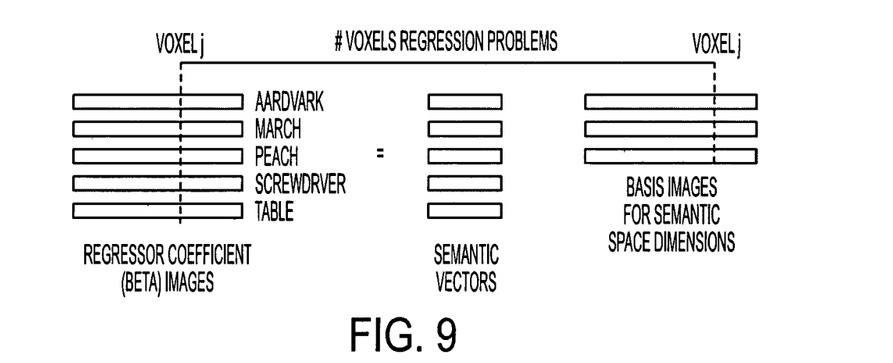
FIG. 9 illustrates an embodiment of learning basis images given regressor coefficient images for each stimulus produced with a general linear model and the corresponding semantic vectors.
Figure 10:
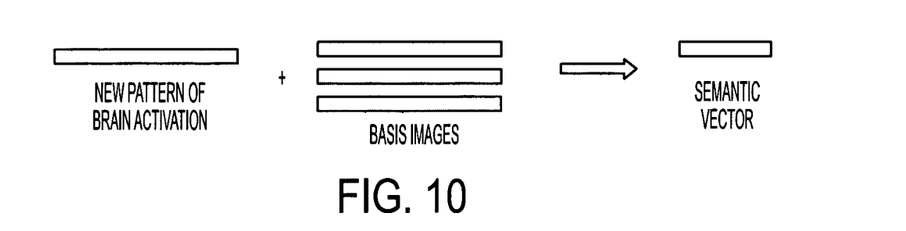
FIG. 10 illustrates an embodiment of using basis images to decode semantic vectors from new brain images.

FIGS. 8-10 illustrate an embodiment of generating natural language representations of mental content from functional brain images. In this embodiment, the basis learning maps a relationship between dimensions of the semantic space and the corresponding brain image data. The mapping associates a semantic vector with a particular brain image. For example, if the subject was reading the word "table," the combined modules obtain a semantic vector for the word "table." Using the semantic vector and the brain image associated with reading the word, the combined modules learn a mapping of the semantic vector to the brain image. The semantic vector decoding inverts that relationship to decode a semantic vector from new brain images.

Both the basis learning and the semantic vector decoding modules require brain images that can be associated with a particular stimulus. The subject is exposed to stimuli at given times, referred to as events, and imaging data is extracted as an image that reflects the effect of the event in the pattern of activation across the brain. However, each time point in the fMRI data includes a recorded convolution in the data due to the mental state of the subject at several preceding time points. In an embodiment, a general linear model (GLM) approach is provided where each event is modeled as a binary time series (e.g., a value of 1 or on if the event is present, and a value of 0 or off otherwise). The binary time series is used to identify voxels in the image that respond to each event type. The result of this approach is one image per event type including the magnitude of the response at each voxel. As such, the GLM approach is a voxelwise regression in terms of the variables of the binary time series.

FIG. 8 illustrates an embodiment of generating brain images reflecting the brain response to specific events (e.g., exposure to stimuli), using a general linear model. Using GLMs with event regressor coefficient images for individual words and/or sentences, brain images associated with each event type are identified. Given that each event type is also represented by a vector in a semantic space, basis images are identified for each dimension in the semantic space, as illustrated in FIG. 9. Each basis image is a spatial pattern of brain activation, reflecting the activation produced by the presence of the corresponding semantic feature. The basis images are then used with new brain images to decode semantic vectors from the images, as illustrated in FIG. 10. The GLM approach is indirect, as individual words trigger semantic representations, and the semantic representations are decoded to generate a text output.

For example, a subject reads words in succession while capturing functional brain imaging data. Instead of a series of events per se, vectors of continuous variables are generated. The effect of the value of each variable across the pattern of brain activation is estimated (much as would be done for the presence of an event) and the estimation is used to infer that vector from new brain imaging data.

Figure 11:
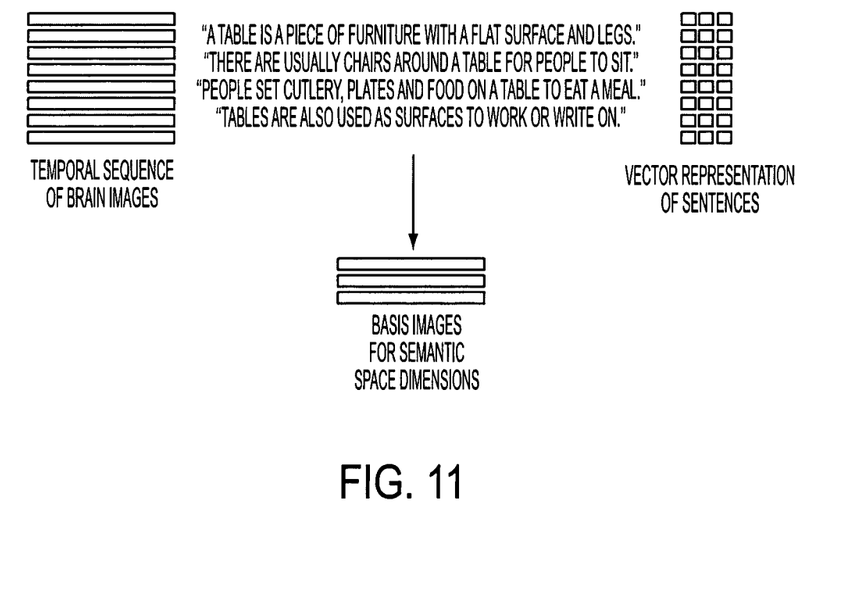
FIG. 11 illustrates an embodiment of a combined method for directly extracting basis images for semantic dimensions, given a temporal sequence of images and a temporal sequence of semantic vectors corresponding to the stimuli shown.

In an alternative embodiment, the basis learning module and the semantic vector decoding module are combined. In this embodiment, semantic vectors corresponding to the stimuli being shown to a subject are produced directly, as illustrated in FIG. 11. The basis learning module and the semantic vector decoding module are combined into a module that is calibrated on the same brain image data, and which is then applied to new brain imaging data to produce semantic vectors.

The first stage can be treated as a multiple regression problem in the temporal domain. The common activity of all trials when performing tasks is modeled using one traditional binary value regressor (e.g., taking the value 1 when the experimental task is being carried out, a stimulus presented, and taking the value 0 otherwise). In addition, one regressor per dimension of the semantic space is modeled. At each time point, the value of the k-th semantic regressors is set to the semantic features $z_k(s)$ of the stimulus s presented at this time or set to zero for inter-trial intervals and fixation periods. A total of K dimensions in the semantic space will generate K different semantic regressors.

The task regressor and semantic regressors are then convolved with a haemodynamic response function (HRF) h. If the head motion is found very significant during the pre-processing, motion parameters (e.g., usually 6 degrees) from motion correction can be also included as confounds in the GLM. Therefore, for each voxel v the time series of BOLD signal is modeled as:

$$y^{(v)} = \beta_{task}^{(v)} x_{task} + \beta_1^{(v)} x_1 + \ldots + \beta_k^{(v)} x_k + \ldots + \beta_K^{(v)} x_K + \beta_{M_1}^{(v)} x_{M_1} + \ldots + \beta_{M_6}^{(v)} x_{M_6} + \beta_0^{(v)},$$

in which $x_{task}$ is the task regressor and $X_k = h*[0, \ldots, z_k(s_1), \ldots, z_k(s_T), 0, \ldots]^T$ represents the regressor for the k-th dimension of the semantic space. The bias term $\beta_0^{(v)}$ can be ignored if all variables are centered at zero. Multiple regression is performed to obtain optimal estimation of all $\beta$ values for all voxels. These $\beta$ values of all voxels constitute a set of basis images, which models the activities associated with different dimensions in semantic space. Assuming a total of m voxels, the image basis can be expressed in matrix form as:

$$B = [\beta^{(1)}, \ldots, \beta^{(m)}] = \begin{bmatrix} \beta_1^{(1)} & \ldots & \beta_1^{(m)} \\ \beta_2^{(1)} & \ldots & \beta_2^{(m)} \\ \vdots & \vdots & \vdots \\ \beta_K^{(1)} & \ldots & \beta_K^{(m)} \end{bmatrix} = [b_1, b_2, \ldots, b_K]^T$$

The second stage is to predict semantic vector for a new image. A new brain activation pattern can be expressed as a linear combination of basis images. Therefore, the decoding of a new image is to estimate the weight of each basis image in the liner combination, which can be calculated by a multiple regression in the spatial domain. Similar to the model in the temporal domain, the testing functional images at t-th TR is modeled as:

$$y_t = b_{task} x_{task,t} + b_1 x_{1,t} + \ldots + b_K x_{K,t} + b_{M_1} x_{M_1,t} + \ldots + b_{M_6} x_{M_6,t} + b_0$$

in which $X_{1,t} \ldots X_{n,t}$ are the weights associated with different dimensions of semantic space at time t. This analysis is conducted on all TRs of a testing functional run and an estimation of the time series of each semantic regressor $X_k$ is obtained. However, this estimation is not the original semantic vector, so the HRF is deconvolved out to get a better prediction of original semantic features. For each dimension k of the semantic space, the convolution with HRF can be formulated as a production of Toeplitz matrix and original semantic features:

$$x_k = h * z_k = \begin{bmatrix} h_1 & 0 & \ldots & 0 \\ h_2 & h_1 & \ldots & \vdots \\ \vdots & h_3 & \ldots & 0 \\ h_{l-1} & \vdots & \ldots & h_1 \\ h_l & h_{l-1} & \ldots & h_2 \\ 0 & h_l & \ldots & \vdots \\ \vdots & 0 & \ldots & h_{l-1} \\ 0 & 0 & \ldots & h_l \end{bmatrix} \begin{bmatrix} 0 \\ \vdots \\ z_k(s_1) \\ z_k(s_2) \\ z_k(s_2) \\ \vdots \\ 0 \end{bmatrix} = Hz_k,$$

The $z_k$ value is derived using multiple regression. In this analysis, the original signal $z_k$ must match the actual stimulus sequence in the testing block. The original regressor $z_k$ has two special characteristics: (1) some elements are zeroes because no events happen at those time points; and (2) some rows are identical because one event can last for more than one TR. Consequently, the Toeplitz matrix (refer to the result as H*) is refined by: (1) removing columns that correspond to zero-value rows in $z_k$; and (2) combining columns that correspond to the same events. As such, the original regressor $z_k$ becomes $z_k^* = [z_k(s_1), z_k(s_2), \ldots, z_k(s_n)]^T$, which only contains variables corresponding to unique events in the testing block. In this way, the convolution problem is expressed as $z_k = H^* z_k^*$ and the original features of all unique events are estimated by a normal equation:

$$\hat{z}_k^* = (H^{*T} H^*)^{-1} H^{*T} x_k.$$

By conducting the two-act analysis, the pattern of brain activation associated with each dimension of semantic space is directly estimated and the semantic space representations for a series of brain images is inferred.

Figure 12:
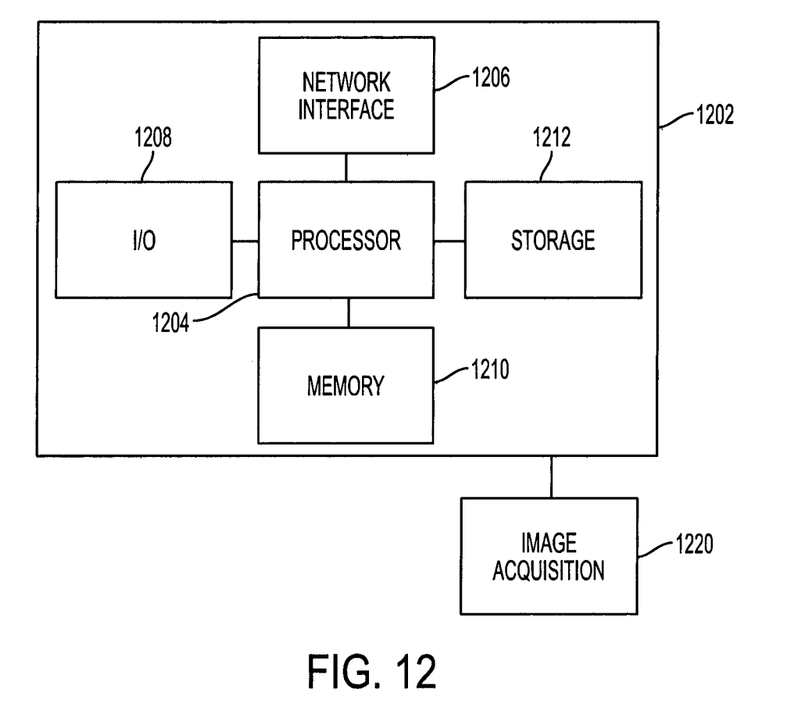
FIG. 12 illustrates an embodiment of a system for generating natural language representations of mental content from functional brain images.

FIG. 12 illustrates an embodiment of a system for generating natural language representations of mental content from functional brain images. For example, the system is implemented on a computer 1202. A high-level block diagram of such a computer is illustrated in FIG. 12. Computer 1202 includes a processor 1204, which controls the overall operation of the computer 1202 by executing computer program instructions which define such operation. The computer program instructions may be stored in a storage device 1212 (e.g., magnetic disk) and loaded into memory 1210 when execution of the computer program instructions is desired. The memory 1210 may be local memory as a component of the computer 1202, or remote memory accessible over a network, such as a component of a server or cloud system. Thus, the acts of the methods may be defined by the computer program instructions stored in the memory 1210 and/or storage 1212 and controlled by the processor 1204 executing the computer program instructions. An image acquisition device 1220, such as a scanner, functional imaging system or fMRI scanner, can be connected to the computer 1202 to input image data to the computer 1202. It is also possible to implement the image acquisition device 1220 and the computer 1202 as one device. It is further possible that the image acquisition device 1220 and the computer 1202 communicate wirelessly through a network.

The computer 1202 also includes one or more network interfaces 1206 for communicating with other devices via a network, such as the image acquisition device 1220. The computer 1202 includes other input/output devices 1208 that enable user interaction with the computer 1202 (e.g., display, keyboard, mouse, speakers, buttons, etc.). Such input/output devices 1208 may be used in conjunction with a set of computer programs as an annotation tool to annotate volumes received from the image acquisition device 1220.

One skilled in the art will recognize that an implementation of an actual computer could contain other components as well, and that FIG. 12 is a high level representation of some of the components of such a computer for illustrative purposes. This technology can, in principle, be used with any quantification of the content of any modality of brain imaging into vectors, where there is a desire to produce a human intelligible, sequentially structured representation (e.g., automated generation of reports).

Figure 13:
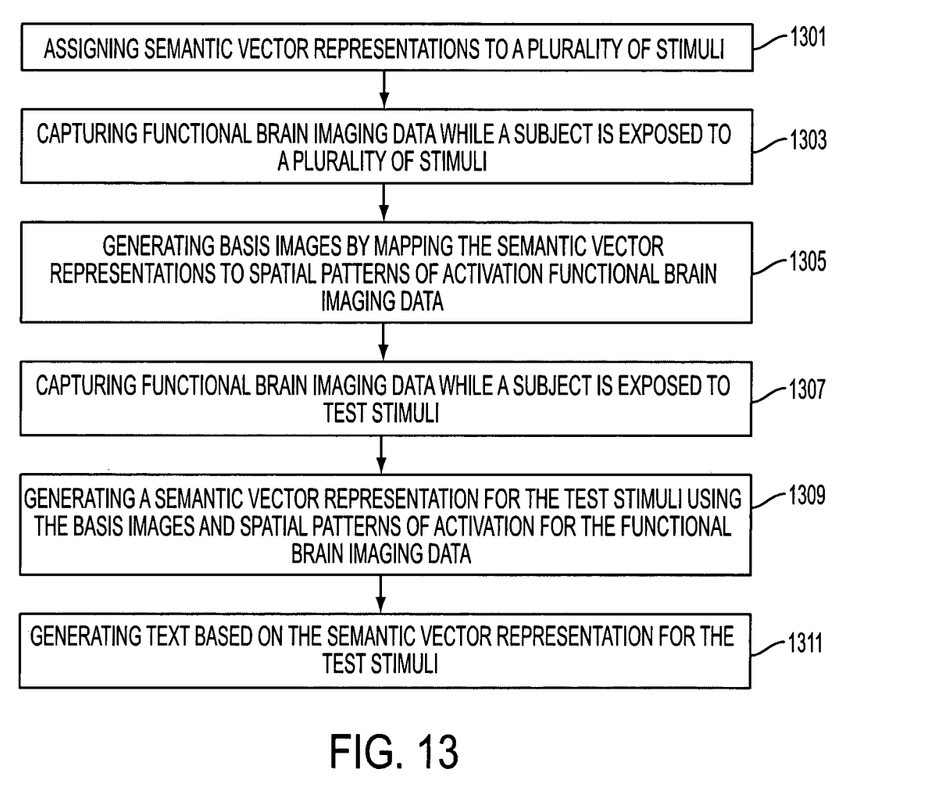
FIG. 13 illustrates a flowchart diagram of an embodiment of a method for generating natural language representations of mental content from functional brain images.

FIG. 13 illustrates a flowchart diagram of an embodiment of a method for generating natural language representations of mental content from functional brain images. The method is implemented by the system of FIG. 12 (discussed above), FIG. 14 (discussed below) and/or a different system. Additional, different or fewer acts may be provided. For example, act 1301, 1303 and 1307 may be omitted. The method is provided in the order shown. Other orders may be provided and/or acts may be repeated. For example, acts 1301-1305 may be repeated to learn more stimuli and/or acts 1307-1311 may be repeated for new stimuli. Further, the acts may be performed concurrently as parallel acts. For example, acts 1303 and 1307 may be performed concurrently to capture brain images for known and unknown stimuli. In an embodiment, acts 1301, 1303 and 1305 are performed to train a system. In another embodiment, acts 1307, 1309 and 1311 are performed by previously a trained system.

At act 1301, semantic vector representations are assigned to a plurality of stimuli. For example, the stimuli is be text, such as words, phrases and/or sentences. Alternatively, the stimuli may be video, sound, smell or any other way to stimuli the senses of a subject. The semantic vector representations are multidimensional and based on context in which the stimuli appears. For example, the semantic vector is a three hundred (300) dimension vector, however the semantic vector may be any number of dimensions.

At act 1303, a first set of functional brain imaging data is captured and/or received while a subject is exposed to the plurality of stimuli. The imaging data is captured using functional magnetic resonance imaging (fMRI). Alternatively, the imaging data is captured using electroencephalography (EEG), magnetoencephalography (MEG), electrocorticography (ECoG), computerized tomography (CT), magnetic resonance (MR) imaging, ultrasound, positron emission tomography, single photon emission computed tomography, or another scanning modality. At act 1305, basis images are generated by mapping semantic vector representations of the plurality of stimuli to spatial patterns of activation in the first set of functional brain imaging data. The basis images are generated by mapping the presence of each dimension in the semantic vector representations to a manifestation of the dimension in the spatial patterns.

At act 1307, a second set of functional brain imaging data are captured and/or received while a subject is exposed to a test stimuli. The second set of the functional brain imaging data are captured using the same imaging modality as the first set of functional imaging data. At act 1309, a semantic vector representation is generated for the test stimuli using the basis images and spatial patterns of activation in the second set of functional brain imaging data. For example, a semantic vector representation for the test stimuli is generated by combining basis images. In this example, combining basis images is a linear combination comprising estimating the weight of each basis image in the linear combination.

At act 1311, text is generated based on the semantic vector representation for the test stimuli. The generated text is a natural language representation of the second set of functional brain imaging data, or another text representation of the stimuli.

Figure 14:
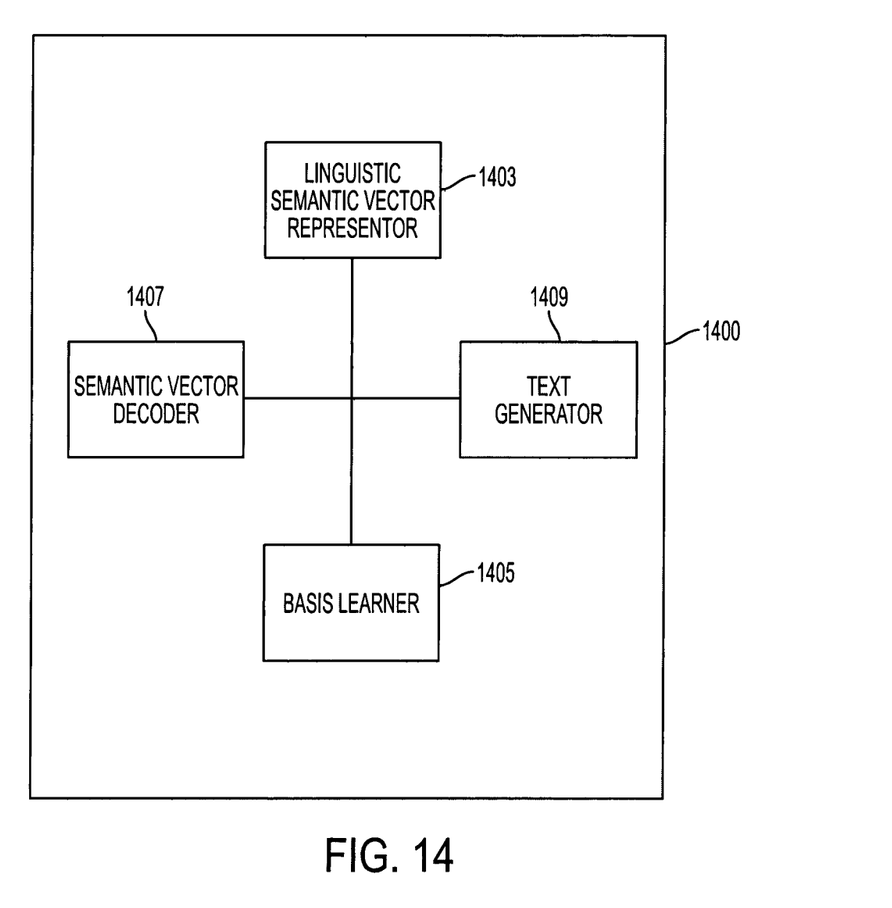
FIG. 14 illustrates an embodiment of a system for generating natural language representations of mental content from functional brain images.

FIG. 14 illustrates an embodiment of a system for generating natural language representations of mental content from functional brain images. The system includes a linguistic semantic vector representor 1403, a basis learner 1405, a semantic vector decoder 1407 and a text generator 1409. Additional, different or fewer elements may be provided. For example, the basis learner 1405 and the semantic vector decoder 1407 may be combined. The elements may be hardware, software or a combination thereof. For example, each element may be configured as a hardware and/or software modules, including: a linguistic semantic vector representation module; a basis learning module; a semantic vector decoding module; and a text generation module.

The linguistic semantic vector representor 1403 is configured to assign semantic vectors to training text. The training text includes words, phrases or sentences. For example, assigning a semantic vector to the training text includes averaging vectors representing each word into a semantic vector for a sentence. The basis learner 1405 is configured to map the semantic vectors to a first set of functional brain imaging data acquired in the presence of the training text. The basis learner may be further configured to identify common characteristics in the functional brain imaging data for overlapping semantic vectors. The semantic vector decoder 1407 is configured to decode a semantic vector from a second set of functional imaging data. For example, the basis learner and the semantic vector decoder are based on a ridge regression. The text generator 1409 is configured to generate a text output based on the decoded semantic vector. For example, the text generator is based on a recurrent neural network. The text output is a sequence of words forming a sentence predicted from the decoded semantic vector, generated based on the semantic vector representation for the test stimuli.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for generating natural language representations of mental content from functional brain images, the method comprising:

capturing a first set of functional brain imaging data while a subject is exposed to a plurality of stimuli comprising training text, wherein the training text is assigned semantic vectors;

decomposing the first set of functional brain imaging data into a weighted combination of basis images, each basis image comprising a spatial pattern of activation;

mapping, for each stimuli, the weighted combination of basis images to corresponding values in each dimension of a semantic vector representing the respective stimuli;

capturing a second set of functional brain imaging data while a subject is exposed to a test stimuli;

identifying a linear combination of basis images in the second set of functional brain imaging data;

decoding a semantic vector representation for the test stimuli by estimating a weight of each basis image in the linear combination of basis images; and generating a text output based on the decoded semantic vector.

2. The method of claim 1 wherein semantic vector representations of the plurality of stimuli are based on context in which the stimuli appears.

3. The method of claim 1 wherein the generated text is a natural language representation of the second set of functional brain imaging data.

4. The method of claim 1 wherein the semantic vectors are multidimensional.

5. A system for generating natural language representations of mental content from functional brain images, the system comprising:

a linguistic semantic vector representor configured to assign semantic vectors to training text;

a basis learner configured to decompose a first set of functional brain imaging data acquired in the presence of the training text into a weighted combination of basis images, each basis image comprising a spatial pattern of activation and map, for the training text, the weighted combination of basis images to corresponding values in each dimension of a semantic vector representing the respective text of the training text;

a semantic vector decoder configured to identify a linear combination of basis images in a second set of functional brain imaging data and decode a semantic vector representation by estimating a weight of each basis image in the linear combination of basis images; and a text generator configured to generate a text output based on the decoded semantic vector.

6. The system of claim 5 wherein the training text comprises words, phrases or sentences.

7. The system of claim 5 wherein assigning a semantic vector to the training text comprises averaging vectors representing each word in a sentence.

8. The system of claim 5 wherein the basis learner is further configured to identify common characteristics in the functional brain imaging data for overlapping semantic vectors.

9. The system of claim 5 wherein the basis learner and the semantic vector decoder are based on a ridge regression.

10. The system of claim 5 wherein the text generator is based on a recurrent neural network.

11. The system of claim 5 wherein the text output is a sequence of words forming a sentence predicted from the decoded semantic vector.

12. A method for generating natural language representations of mental content from functional brain images, the method comprising:

assigning multidimensional linguistic semantic vector representations to a plurality of training text;

decomposing a first set of functional brain imaging data acquired in the presence of the training text into a weighted combination of basis images, each basis image comprising a spatial pattern of activation;

mapping the weighted combination of basis images to corresponding values in each dimension of a semantic vector representing the respective text of the training text;

identifying a linear combination of basis images in a second set of functional brain imaging data;

decoding a semantic vector representation by estimating a weight of each basis image in the linear combination of basis images; and generating text based on the semantic vector representation.

13. The method of claim 12, wherein the training text comprise words, phrases or sentences.

14. The method of claim 12, wherein the generated text comprises a word, phrase or sentence.

* * * * *